United States Patent [19]

Elbe et al.

[11] Patent Number: 4,940,798
[45] Date of Patent: Jul. 10, 1990

[54] SUBSTITUTED AZOLYLVINYL KETONES AND CARBINOLS AS FUNGICIDES AND PLANT GROWTH REGULATORS

[75] Inventors: Hans-Ludwig Elbe; Wolf Reiser; Erik Regel, all of Wuppertal; Karl H. Büchel, Burscheid; Paul Reinecke, Leverkusen; Wilhelm Brandes, Leichlingen; Klaus Lürssen, Bergisch-Gladbach; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 100,650

[22] Filed: Sep. 24, 1987

Related U.S. Application Data

[62] Division of Ser. No. 754,788, Jul. 12, 1985, Pat. No. 4,728,356, which is a division of Ser. No. 518,866, Aug. 1, 1983, abandoned.

[30] Foreign Application Priority Data

Aug. 5, 1982 [DE] Fed. Rep. of Germany ....... 3229274

[51] Int. Cl.$^5$ ................... C07D 249/08; C07D 233/60
[52] U.S. Cl. .................................. 548/268.4; 548/101; 548/341
[58] Field of Search .............. 548/101, 262, 336, 341; 546/276, 278

[56] References Cited

U.S. PATENT DOCUMENTS 4,517,367  5/1985  Skötsch et al. ...................... 548/262
4,549,900 10/1985  Kramer et al. ......................... 71/92

FOREIGN PATENT DOCUMENTS 040345 11/1981 European Pat. Off. ............ 548/262
044993  3/1982 European Pat. Off. ............ 548/262
3028337  3/1982 Fed. Rep. of Germany ...... 548/262

*Primary Examiner*—Glennon H. Hollrah
*Assistant Examiner*—Patricia L. Morris
*Attorney, Agent, or Firm*—Sprung Horn Kramer & Woods

[57] ABSTRACT

A substituted azolylvinyl ketone or carbinol of the formula

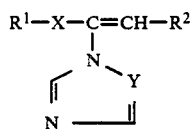

in which
R$^1$ represents optionally substituted cycloalkyl with 3 to 5 carbon atoms, substituted cyclohexyl or the grouping

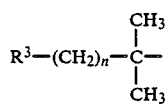

wherein
R$^3$ represents optionally substituted phenyl, alkenyl, alkinyl, cyano or the grouping —Z—R$^4$,
wherein
R$^4$ represents alkyl, halogenoalkyl, optionally substituted phenyl or optionally substituted phenylalkyl and
Z represents O, S, SO or SO$_2$,
n represents a number from 0 to 2,
R$^2$ represents alkyl, alkenyl, alkinyl, in each case optionally substituted phenyl or phenylalkyl, or in each case optionally substituted cycloalkyl, cycloalkylalkyl, cycloalkenyl, cycloalkenylalkyl, bicycloalkyl or bicycloalkenyl, but R$^2$ does not represent optionally substituted phenyl at the same time as R$^1$ represents optionally substituted cycloalkyl with 3 to 5 carbon atoms or substituted cyclohexyl or R$^3$ represents optionally substituted phenyl,
X represents the CO or CH(OH) group and
Y represents a nitrogen atom or the CH group, or an addition product thereof with an acid or metal salt. The products are active in combating fungi and in regulating the growth of plants.

3 Claims, No Drawings

SUBSTITUTED AZOLYLVINYL KETONES AND CARBINOLS AS FUNGICIDES AND PLANT GROWTH REGULATORS

This is a division of application Ser. No. 754,788, filed Jul. 12, 1985, now U.S. Pat. No. 4,728,356, which ia a division of application Ser. No. 518,866, filed Aug. 1, 1983, now abandoned.

The present invention relates to new substituted azolyvinyl ketones and carbinols, several processes for their preparation and their use as fungicides and plant growth regulators.

It has already been disclosed that certain 1-vinyl-traizolyl-(halogeno)-tert.-butyl ketones and carbinols have good fungicidal properties (compare DE-OS (German Published Specification) 2,906,061, DE-OS (German Published Specification) 2,938,422, U.S. Ser. No. 259,303, filed Apr. 30, 1981, now pending, DE-OS (German Published Specification ) 2,838,847 and Japanese Patent Application J5 31 30 661). However, the action of these compounds is not always completely satisfactory, especially when low amounts and concentrations are applied.

New substituted azolylvinyl ketones and carbinols of the general formula

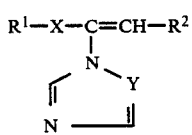

in which
R$^1$ represents optionally substituted cycloalkyl with 3 to 5 carbon atoms, substituted cyclohexyl or the grouping

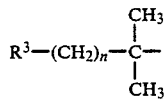

wherein
R$^3$ represents optionally substituted phenyl, alkenyl, alkinyl, cyano or the grouping —Z—R$^4$,
wherein
R$^4$ represents alkyl, halogenoalkyl, optionally substituted phenyl or optionally substituted phenylalkyl and
Z represents O, S, SO or SO$_2$,
n represents a number from 0 to 2,
R$^2$ represents alkyl, alkenyl, alkinyl, in each case optionally substituted phenyl or phenylalkyl, or in each case optionally substituted cycloalkyl, cycloalkylalkyl, cycloalkenyl, cycloalkenylalkyl, bicycloalkyl or bicycloalkenyl, but R$^2$ does not represent optionally substituted phenyl at the same time as R$^1$ represents optionally substituted cycloalkyl with 3 to 5 carbon atoms or substituted cyclohexyl or R$^3$ represents optionally substituted phenyl,
X represents the CO or CH(OH) group and
Y represents a nitrogen atom or the CH group, and acid addition salts and metal salt complexes thereof, have been found.

The compounds of the formula (I) according to the invention occur in the geometric isomers E (trans) and Z (cis). In the E,Z nomenclature, the substituents on the double bond are arranged in order of decreasing priority in accordance with the Cahn-Ingold-Prelog rule. If the preferred substituents are on the same side of the double bond, the compound has the Z configuration (derived from zusammen (together)), and if they are on opposite sides, the compound has the E configuration (derived from entgegen (opposite to)).

The compounds of the formula (I) according to the invention where X=CH(OH) also have two asymmetric carbon atoms; in this case, they can exist in the form of the two geometric isomers (threo and erythro form), which can be obtained in varying proportions. In both cases, they are in the form of optical isomers.

It has furthermore been found that the substituted azolylvinyl ketones and carbinols of the formula (I) and acid addition salts and metal salt complexes thereof are obtained by a process in which (a) ketoenamines of the formula

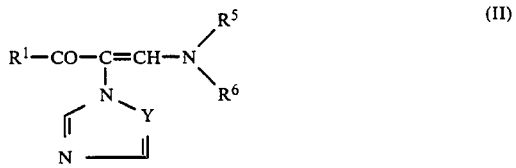

in which
R$^1$ and Y have the abovementioned meaning and R$^5$ and R$^6$ are identical or different and represent alkyl with 1 to 4 carbon atoms; or, together with the N atom to which they are bonded, represent piperidinyl, pyrrolidinyl or morpholinyl, in each case optionally mono- to tri-substituted by alkyl with 1 to 4 carbon atoms, are reacted with organomagnesium compounds of the formula

in which
R$^2$ has the abovementioned meaning and Hal represents halogen,
in the presence of a solvent and, if appropriate, in the presence of an inert gas, or (b) azolyl ketones of the formula

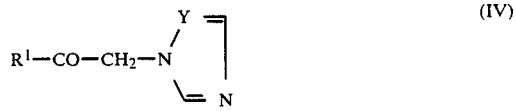

in which
R$^1$ and Y have the abovementioned meaning, are reacted with aldehydes of the formula

in which
R$^2$ has the abovementioned meaning, in the presence of a solvent and in the presence of a catalyst, and (c) if desired, the substituted azolylvinyl ketones according to the invention of the formula

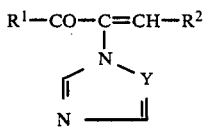

$$R^1\text{—CO—C}=\text{CH—}R^2 \quad (Ia)$$

$R^1$, $R^2$ and Y have the abovementioned meaning, obtained by processes (a) and (b) are reduced in a generally customary manner.

If desired, an acid or a metal salt can be added onto the compounds of the formula (I) thus obtained.

Finally, it has been found that the new substituted azolylvinyl ketones and carbinols of the formula (I) and acid addition salts and metal salt complexes thereof have powerful fungicidal and powerful plant growth regulating properties.

The new substituted azolylvinyl ketones and carbinols of the formula (I) are also interesting intermediates for the preparation of other plant protection agents. In the case of the keto derivatives, the keto group can be reduced to a —CH(OH)— group or a —CR(OH)— group. Furthermore, functional derivatives of the keto group can be obtained by an appropriate reaction, such as, for example, oximes and oxime ethers, hydrazones and ketals. The carbinol derivatives can be converted into the corresponding ethers on the hydroxyl group in the customary manner. Furthermore, acyl or carbamoyl derivatives of the compounds of the formula (I) can be obtained by reaction with, for example, acylhalides or carbamoyl chlorides in a manner which is known in principle.

Surprisingly, the compounds according to the invention have a better fungicidal action than the 1-vinyl-triazolyl-(halogeno)-tert.-butyl ketones and carbinols which are known from the prior art and are closely related compounds from a chemical and biological point of view. The compounds according to the invention also display good plant growth regulating properties. The active compounds according to the invention thus represent an enrichment of the art.

The formula (I) provides a general definition of the substituted azolyvinyl ketones and carbinols according to the invention. In this formula, preferably, $R^1$ represents cycloalkyl with 3 to 5 carbon atoms which is optionally monosubstituted or polysubstituted by identical or different substituents, or substituted cyclohexyl, possible substituents in each case being: alkyl with 1 to 4 carbon atoms and halogen; or the grouping

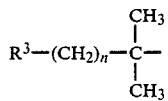

$R^3$ represents phenyl which is optionally monosubstituted to polysubstituted by identical or different substituents, preferred substituents which may be mentioned being: halogen, alkyl with 1 to 4 carbon atoms, alkoxy and alkylthio with in each case 1 to 4 carbon atoms, alkyl and dialkylamino with in each case 1 to 4 carbon atoms in each alkyl part, and furthermore halogenoalkyl, halogenoalkoxy and halogenoalkylthio with in each case 1 or 2 carbon atoms and 1 to 5 identical or different halogen atoms, such as fluorine and chlorine atoms, and phenyl and phenoxy which are optionally substituted by halogen and alkyl with 1 or 2 carbon atoms; or, furthermore, straight-chain or branched alkenyl with 2 to 4 carbon atoms or alkinyl with 3 to 5 carbon atoms; or cyano or the grouping —Z—$R^4$;

$R^4$ represents straight-chain or branched alkyl with 1 to 6 carbon atoms; halogenoalkyl with 1 to 4 carbon atoms and 1 to 5 identical or different halogen atoms, such as fluorine and chlorine atoms; or phenyl or phenyalkyl with 1 or 2 carbon atoms in the alkyl part, each of which is optionally monosubstituted or polysubstituted by identical or different substituents, preferred possible substituents on the phenyl in each case being the substituents on phenyl already mentioned in the case of $R^3$;

$R^2$ represents straight-chain or branched alkyl with 1 to 12 carbon atoms; straight-chain or branched alkenyl or alkinyl with in each case 2 to 7 carbon atoms; phenyl or phenylalkyl with 1 to 4 carbon atoms in the alkyl part, each of which is optionally monosubstituted or polysubstituted by identical or different substituents, preferred possible substituents on the phenyl in each case being those substituents on phenyl which have already been mentioned in the case of $R^3$; or, furthermore, cycloalkyl with 3 to 12 carbon atoms, cycloalkylalkyl with 3 to 7 carbon atoms in the cycloalkyl part and 1 to 4 carbon atoms in the alkyl part, cycloalkenyl with 3 to 12 carbon atoms, cycloalkenylalkyl with 3 to 7 carbon atoms in the cycloalkenyl part and 1 to 4 carbon atoms in the alkyl part, bicycloalkyl with 2 to 24 carbon atoms or bicycloalkenyl with 4 to 24 carbon atoms, each of which is optionally monosubstituted or polysubstituted by identical or different substituents from the group comprising alkyl with 1 to 4 carbon atoms and halogen; but $R^2$ does not represent optionally substituted phenyl at the same time as $R^1$ represents optionally substituted cycloalkyl with 3 to 5 carbon atoms or substituted cyclohexyl or $R^3$ represents optionally substituted phenyl; and X, Y and Z and the index n have the meanings given in the definition of the invention.

Particularly preferred compounds of the formula (I) are those in which $R^1$ represents cyclopropyl or cyclopentyl which is optionally monosubstituted or di- or tri-substituted by identical or different constituents, or cyclohexyl which is optionally monosubstituted or di- or tri-substituted by identical or different substituents, possible substituents in each case being: methyl, ethyl, isopropryl, tert.-butyl, chlorine or bromine, or the grouping

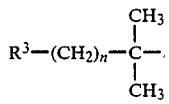

$R^3$ represents phenyl which is optionally monosubstituted or di- or tri-substituted by identical or different substituents, preferred substituents which may be mentioned being: fluorine, chlorine, methyl, isopropyl, tert.-butyl, methoxy, methylthio, isopropoxy, trifluoromethyl, trifluoromethoxy, trifluoromethylthio, methylamino, dimethylamino and phenyl or phenoxy which is optionally substituted by fluorine, chlorine and methyl; or, furthermore, vinyl, propargyl, cyano or the grouping —Z—R⁴;

R⁴ represents straight-chain or branched alkyl with 1 to 4 carbon atoms, or phenyl or benzyl which is in each case optionally monosubstituted or di- or tri-substituted by identical or different substituents, preferred possible substituents on the phenyl in each case being the substituents on phenyl which have already been mentioned in the case of R³;

R² represents straight-chain or branched alkyl with 1 to 8 carbon atoms or straight-chain or branched alkenyl or alkinyl with in each case 2 to 4 carbon atoms; or, furthermore, phenyl or phenylalkyl with 1 or 2 carbon atoms in the alkyl part, each of which is optionally monosubstituted or di- or tri-substituted by identical or different substituents, preferred possible substituents on the phenyl being the substituents on phenyl which have already been mentioned in the case of R³; or, furthermore, cyclopropyl, cyclobutyl, cyclopentyl, cyclohexyl, cyclopropylmethyl, cyclobutylmethyl, cyclopentylmethyl, cyclohexylmethyl, cycloheptylmethyl, cycloalkenyl with 3 to 7 carbon atoms, cycloalkenylmethyl with 3 to 7 carbon atoms in the cycloalkenyl part, bicycloalkyl with 5 to 12 carbon atoms or bicycloalkenyl with 5 to 12 carbon atoms, each of which is optionally monosubstituted or di- or tri-substituted by identical or different substituents from the group comprising methyl, ethyl, isopropyl, fluorine and chlorine; but R² does not represent optionally substituted phenyl at the same time as R¹ represents optionally substituted cycloalkyl with 3 to 5 carbon atoms or substituted cyclohexyl or R³ represents optionally substituted phenyl; and X, Y and Z and the index n have the meaning given in the definition of the invention.

Preferred compounds according to the invention also include addition products of acids and those azolylvinyl ketones and carbinols of the formula (I) in which R¹, R², X and Y have the meanings which have already been mentioned as preferred for these radicals.

Preferred acids which can be added on include hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Other preferred compounds according to the invention are addition products of salts of metals of main groups II to IV and of sub-groups I and II and IV to VIII and those azolylvinyl ketones and carbinols of the formula (I) in which R¹, R², X and Y have the meanings already given as preferred for these radicals.

In this context, salts of copper, zinc, manganese, magnesium, tin, iron and nickel are particularly preferred. Possible anions of these salts are those which are derived from acids which lead to physiologically acceptable addition products. In this connection, particularly preferred acids of this type are the hydrogen halide acids, such as, for example, hydrochloric acids and hydrobromic acid, and furthermore phosphoric acid, nitric acid and sulphuric acid.

If, for example, 1-(4-chlorophenyl)-2,2-dimethyl-5-dimethylamino-4-(1,2,4-triazol-1-yl)-4-penten-3-one and n-propyl-magnesium bromide are used as starting substances, the course of the reaction can be represented by the following equation (process a):

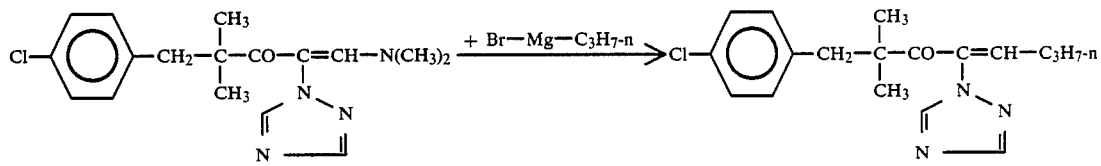

If, for example, 1-(4-chlorophenyl)-2,2-dimethyl-4-(1,2,4-triazol-1-yl)-3-butanone and cyclohexanecarbaldehyde are used as starting substances, the course of the reaction can be represented by the following equation (process b):

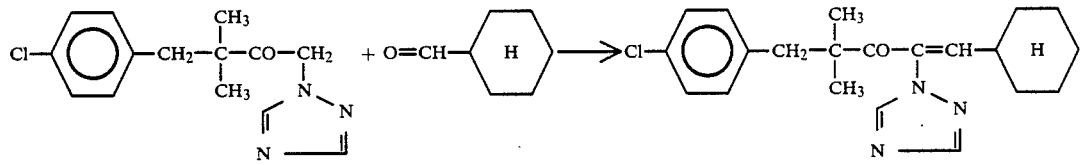

If, for example, 1-(4-chlorophenyl)-2,2-dimethyl-4-(1,2,4-triazol-1-yl)-4-octan-3-one is used as the starting substance and sodium borohydride is used as the reducing agent, the course of the reaction can be represented by the following equation (process c):

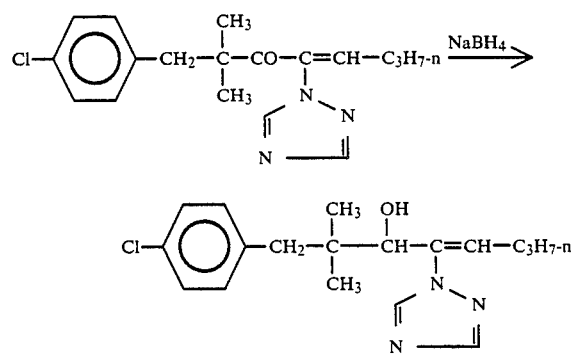

The formula (II) provides a general definition of the ketoenamines to be used as starting substances for process (a) according to the invention. In this formula, $R^1$ preferably represents those radicals which have already been mentioned as preferred for this substituent in connection with the description of the substances of the formula (I) according to the invention. $R^5$, $R^6$ and Y have the meanings given in the definition of the invention.

The ketoenamines of the formula (II) are the subject of patent application Ser. No. filed , now pending, (Le A 21 845-US), and are obtained by reacting azolyl ketones of the formula

in which
$R^1$ and Y have the abovementioned meaning, with amide acetals or aminal esters of the formulae

in which
$R^5$ and $R^6$ have the abovementioned meaning and
$R^7$ represents alkyl with 1 to 4 carbon atoms, in a manner which is in itself known, in the presence of an inert organic solvent, such as, for example, an aromatic hydrocarbon, and such as, in particular, an amide acetal or aminal ester of the formula (VIa) or (VIb) employed in excess, at the boil (in this context, compare also Chem. Ber. 101, 41–50 (1968); J. Org. Chem. 43, 4248–50 (1978) and the preparation examples).

Azolyl ketones of the formula (IV) are known (in this context, compare U.S. Ser. No. 291,699, filed Aug. 10, 1981, DE-OS (German Published Specification) 2,906,061, DE-OS (German Published Specification) 3,028,330, U.S. Ser. No. 481,615, filed Apr. 4, 1983, now pending, U.S. Ser. No. 438,086, filed Nov. 1, 1982, now pending, and U.S. Ser. No. 438,087, filed Nov. 1, 1982, now pending, and they can be prepared by customary methods, by reacting the corresponding halogeno ketones with 1,3,4-triazole or imidazole in the presence of an acid-binding agent.

The amide acetals and aminal esters of the formulae (VIa) and (VIb) are generally known compounds of organic chemistry (compare, for example, Chem. Ber. 101, 41–50 (1968) and J. Org. Chem. 43, 4248–50 (1978)); they can be prepared by the processes described in these references.

The formula (III) provides a general definition of the organomagnesium compounds also to be used as starting substances for process (a) according to the invention. In this formula, $R^2$ preferably represents those radicals which have already been mentioned as preferred for these substituents in connection with the description of the substances of the formula (I) according to the invention. Hal preferably represents chlorine or bromine.

The organomagnesium compounds of the formula (III) are generally known compounds of organic chemistry.

The formula (IV) provides a general definition of the azolyl ketones to be used as starting substances for process (b) according to the invention. In this formula, $R^1$ and Y preferably represent those radicals which have already been mentioned as preferred for these substituents in connection with the description of the substances of the formula (I) according to the invention.

The formula (V) provides a general definition of the aldehydes also to be used as starting substances for process (b) according to the invention. In this formula, $R^2$ preferably represents those radicals which have already been mentioned as preferred for this substituent in connection with the description of the substances of the formula (I) according to the invention.

The aldehydes of the formula (V) are generally known compounds of organic chemistry.

The azolylvinyl ketones to be used as starting substances for process (c) according to the invention are substances according to the invention.

Preferred possible solvents for the reaction according to the invention in process (a) are inert organic solvents, in the pure form or as mixtures. These include, preferably, ethers, such as diethyl ether, methyl ethyl ether, tetrahydrofuran or dioxane, aliphatic and aromatic hydrocarbons, such as, in particular, benzene, toluene or xylene, and hexamethylphosphoric acid triamide.

The reaction temperatures can be varied within a substantial range in carrying out process (a) according to the invention. In general, the reaction is carried out between $-50°$ and $+150°$ C., preferably between $-20°$ and $+120°$ C.

The reaction according to the invention in process (a) can be carried out in the presence of an inert gas, such as, for example, nitrogen or helium.

In carrying out process (a) according to the invention, 1 to 1.5 mols of organomagnesium compounds of the formula (III) are preferably employed per mol of ketoenamine of the formula (II). The compounds of the formula (I) are isolated in the customary manner.

Preferred possible solvents for process (b) according to the invention are inert organic solvents. These include, preferably, alcohols, such as methanol and ethanol; ethers, such as tetrahydrofuran and dioxane; aliphatic and cycloaliphatic hydrocarbons, such as hexane and cyclohexane; aromatic hydrocarbons, such as benzene, toluene and cumene; and halogenated aliphatic and aromatic hydrocarbons, such as methylene chloride, carbon tetrachloride, chloroform, chlorobenzene and dichlorobenzene.

Process (b) according to the invention is carried out in the presence of a catalyst. It is possible to use all the acid and, in particular, basic catalysts, and buffer mixtures thereof, which can usually be used. Preferred catalysts include Lewis acids, such as, for example, boron trifluoride, boron trichloride, tin tetrachloride or titanium tetrachloride; organic bases, such as pyridine and piperidine; and, in particular, piperidine acetate.

The reaction temperatures can be varied within a substantial range in carrying out process (b) according to the invention. In general, the reaction is carried out between 20° and 160° C., preferably at the boiling point of the particular solvent.

In carrying out process (b) according to the invention, 1 to 1.5 mols of aldehyde of the formula (V) and catalytic to 0.2 mol amounts of catalyst are employed per mol of triazole-ketone of the formula (IV). The compounds of the formula (I) are isolated in the customary manner.

The reduction according to the invention in process (c) is carried out in the customary manner, for example by reaction with complex hydrides, if appropriate in the presence of a diluent, or by reaction with aluminum isopropylate in the presence of a diluent.

If complex hydrides are used, possible diluents for this reaction according to the invention are polar organic solvents. These include, preferably, alcohols, such as methanol, ethanol, butanol or isopropanol, and ethers, such as diethyl ether or tetrahydrofuran. The reaction is in general carried out at 0° to 30° C., preferably at 0° to 20° C. For this reaction, about 1 reaction equivalent of a complex hydride, such as sodium borohydride or lithium alanate, is employed per mol of the ketone of the formula (Ia). To isolate the reduced compounds of the formula (I), the residue is taken up in dilute hydrochloric acid and the mixture is then rendered alkaline and extracted with an organic solvent. Further working up is effected in the customary manner.

If aluminum isopropylate is used, preferred possible diluents for this relation according to the invention are alcohols, such as isopropanol, or inert hydrocarbons, such as benzene. The reaction temperatures can again be varied within a substantial range; in general, the reaction is carried out at between 20° and 120° C., preferably at 50° to 100° C. For carrying out the reaction, about 1 to 2 mols of aluminum isopropylate are employed per mol of the ketone of the formula (Ia). To isolate the reduced compounds of the formula (I), the excess solvent is removed by distillation in vacuo and the aluminum compound formed is dissociated with dilute sulphuric acid or sodium hydroxide solution. Further working up is effected in the customary manner.

Those acids which have already been mentioned as preferred acids in connection with the description of the acid addition salts according to the invention are preferably used for the preparation of acid addition salts of the azolyvinyl ketones and carbinols of the formula (I).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if necessary, purified by washing with an inert organic solvent.

Salts of those anions and cations which have already been mentioned as preferred in connection with the description of the metal salt complexes according to the invention are preferably used for the preparation of metal salt complexes of axolyvinyl ketones and carbinols of the formula (I).

The metal salt complexes of the compounds of the formula (I) can be obtained in a simple manner by customary processes, thus, for example, by dissolving the metal salt in alcohol, for example ethanol, and adding the solution to the compound of the formula (I). Metal salt complexes can be isolated in a known manner, for example by filtration, and if necessary purified by recrystallization.

The active compounds according to the invention exhibit a powerful microbicidal action and can be employed in practice fro combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases; thus, for example, against the powdery mildew of barley causative organism (Erysiphe graminis), the brown rust on wheat causative organism (Puccinia recondita), the spot blotch disease of cereals causative organism (Cochliobolus sativus), the brown spot disease on wheat causative organism (Leptoshaeria nodorum) or the leaf spot disease on barley causative organism (Pyrenophora teres); and furthermore for combating Venturia species, such as against the apple scab causative organism (Venturia inaequalis), and rice diseases, such as Pyricularia and Pellicularia.

The active compounds which can be used according to the invention engage in the metabolishm of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibtion of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultganeously lead to a promotion of generative growth, since more assimilates are formed, so that more fruit, or larger fruit, is obtained.

Increases in yield can in some cases be achieved by affecting the plant metabolish, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able t o carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefield gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellant, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysation products. As dispersing agents there are suitable: for example, ligninsulphite waste liquors and methylcellulose.

Adhesives such as carboxymethylcellulose and natural and synthetic polymers in the form of powders, granules or latices, such as gum aragic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are used as plant growth regulators, the amount applied can be varied within a substantial range. In general, 0.01 to 50 kg, preferably 0.05 to 10 kg, are used per hectare of soil surface.

When the substances according to the invention are used as plant growth regulators, they are applied within a preferred period of time, the exact definition of which depends on the climatic and vegetative circumstances.

When the substances according to the invention are used as fungicides, the amount applied can also be varied within a substantial range, depending on the nature of the application. Thus, in the treatment of parts of plants, the concentrations of active compound in the use forms are generally between 1 to 0.0001% by weight, preferably between 0.5 and 0.001% by weight. In the treatment of seed, amounts of active compound of 0.001 to 50 g per kg of seed, preferably 0.01 to 10 g, are generally required. In the treatment of soil, active compound concentrations of 0.00001 to 0.1% by weight, preferably of 0.0001 to 0.2%, are required at the place of action.

The preparation and use of the substances according to the invention are illustrated by the examples which follow.

PREPARATION EXAMPLES

EXAMPLE 1

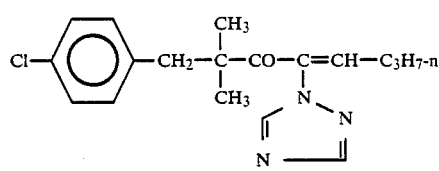

(Process a)

49.9 g (0.15 mol) of 1-(4-chlorophenyl)-2,2-dimethyl-5-dimethylamino-4-(1,2,4-triazol-1-yl)-4-penten-3-one are dissolved in 750 ml of ether, and a solution of 33.9 g (0.23 mol) of n-propyl-magnesium bromide in 100 ml of ether is added dropwise at −20° C. The reaction mixture is subsequently stirred for 1.5 hours, during which it warms to room temperature. The reaction mixture is adjusted to a pH value of 7 to 8 with dilute hydrochloric acid. The organic phase is then separated off, washed with water, dried over sodium sulphate and concentrated. The residue is purified by column chromatography (silica gel; ethyl acetate/cyclohexane=3:1). 30.1 g (60.5% of theory) of 1-(4-chlorophenyl)-2,2-dimethyl-4-(1,2,4-triazol-1-yl)-4-octen-3-one of refractive index $n_D^{20}$ 1.5429 are obtained.

Preparation of the starting material

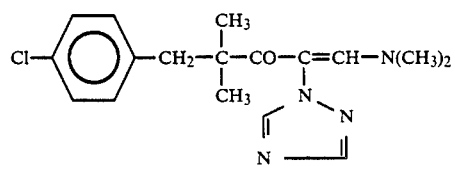

50 g (0.18 mol) of 1-(4-chlorophenyl)-2,2-dimethyl-4-(1,2,4-triazol-1-yl)-3-butanone are heated under reflux with 23.6 g (0.138 mol) of dimethylformamide dimethylacetal for 8 hours. To isolate the end product, the reaction mixture is concentrated in vacuo. 56.5 g (94.4% of theory) of 1-(4-chlorophenyl)-2,2-dimethyl-5-dimethylamino-4-(1,2,4-triazol-1-yl)-4-penten-3-one of refractive index $n^{20}$ 1.5797 are obtained.

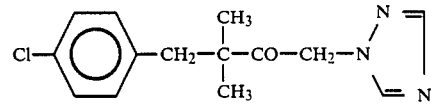

37 (0.13 mol) of 4-bromo-1-(4-chlorophenyl)-2,2-dimethyl-3-butanone, 13.3 g (0.019 mol) of 1,2,4-triazole and 53.8 g (0.39 mol) of potassium carbonate are heated under reflux in 300 ml of acetone for 8 hours. The mixture is allowed to cool, the inorganic residue is filtered off with suction and the filtrate is concentrated. The residue is taken up in chloroform and the mixture is washed with water, dried over sodium sulphate and concentrated. The residue is stirred with diethyl ether, filtered off with suction and dried at 50° C. in vacuo. 18.8 g (52% of theory) of 1-(4-chlorophenyl)-2,2-dimethyl-4-(1,2,4-triazol-1-yl)-3-butanone of melting point 127° C. are obtained.

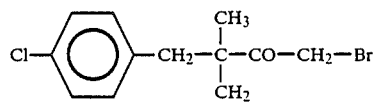

98.8 g (0.6 mol) of bromine are added dropwise to 130 g (0.62 mol) of 1-(4-chlorophenyl)-2,2-dimethyl-3-butanone in 1000 ml of chloroform at room temperature. The reaction mixture is subsequently stirred for 1 hour and is then concentrated. 174.7 g (97.3% of theory) of 4-bromo-1-(4-chlorophenyl)-2,2-dimethyl-3-butanone of refractive index $n_D^{20}$ 1.5570 are obtained.

EXAMPLE 2

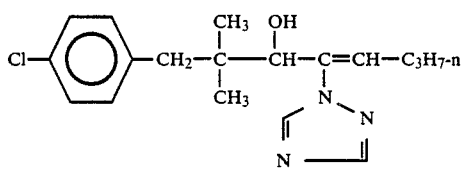

(Process c)

7 g (0.021 mol) of 1-(4-chlorophenyl)-2,2-dimethyl-4-(1,2,4-triazol-1-yl)-4-octen-3-one (Example 1) are dissolved in 100 ml of methanol, and a solution of 0.21 g (0.006 mol) of sodium borohydride in 5 ml of icewater is added dropwise at −10° C. The reaction mixture is subsequently stirred at 0° C. for 1.5 hours and is then adjusted to a pH value of 6 to 7 with dilute hydrochloric acid. The reaction mixture is concentrated by distilling off the solvent in vacuo. The residue is taken up in chloroform and the mixture is washed with water, dried over sodium sulphate and concentrated. 6.5 g (92.9% of theory) of 1-(4-chlorophenyl)-2,2-dimethyl-4-(1,2,4-triazol-1-yl)-4-octen-3-ol of refractive index $n_D^{20}$ 1.5383 are obtained.

EXAMPLE 3

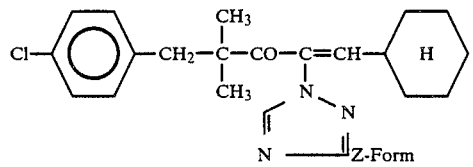

8.2 g (0.03 mol) of 1-(4-chlorophenyl)-2,2-dimethyl-4-(1,2,4-triazol-1-yl)-3-butanone, 3.4 g (0.03 mol) of cyclohexanecarbaldehyde, 1.1 g (0.018 mol) of acetic acid and 0.8 g (0.009 mol) of piperidine are dissolved in 60 ml of toluene and the solution is heated under reflux for 8 hours, using a water separator. The cooled reaction solution is washed with water, the organic phase is extracted with sodium bisulphite solution, the precipitate which has separated out is filtered off with suction and the toluene phase is washed with sodium bicarbonate solution. After drying over sodium sulphate, the solvent is stripped off on a rotary evaporator and the oily residue (11.0 g) is chromatographed on a column, over silica gel using petroleum ether/glacial acetic acid (2:1). The first fractions were combined and the solvent mixture was stripped off on a rotary evaporator.

3.0 g (26.9% of theory) of 1-(4-chlorophenyl)-5-cyclohexyl-2,2-dimethyl-4-(1,2,4-triazol-1-yl)-4-penten-3-one (Z-form) are obtained as a light-colored oil. 20 MHz-NMR, CDCl$_3$ (δ, ppm): 1.12 (s, 6H); 1.20 (m, 6H); 1.70 (m, 5H); 2.90 (s, 2H);, 6.35 (d, 1H); 7.05 (d, 2H); 7.23 (d, 2H); 8.00 (s, 1H) and 8.07 (s, 1H).

The following compounds of the general formula (I)

are obtained in a corresponding manner by the processes described.

| Example No. | R$^1$ | X | Y | R$^2$ | Melting point (°C.) or $n_D^{20}$ |
|---|---|---|---|---|---|
| 4 | 2,6-Cl$_2$-C$_6$H$_3$-OCH$_2$-C(CH$_3$)$_2$- | CO | N | —C$_7$H$_{15}$-n | viscous oil |
| 5 | 2,6-Cl$_2$-C$_6$H$_3$-OCH$_2$-C(CH$_3$)$_2$- | CO | N | —C$_3$H$_7$-i | 36–39 |
| 6 | 4-Cl-C$_6$H$_4$-OCH$_2$-C(CH$_3$)$_2$- | CO | N | —C$_7$H$_{15}$-n | viscous oil |

-continued

| Example No. | R¹ | X | Y | R² | Melting point (°C.) or $n_D^{20}$ |
|---|---|---|---|---|---|
| 7 | 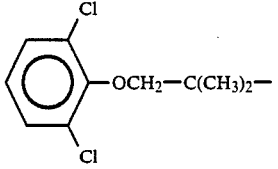 2,6-dichlorophenyl-OCH₂—C(CH₃)₂— | CO | N | —CH₃ | 96 |
| 8 | 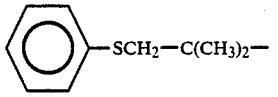 phenyl-SCH₂—C(CH₃)₂— | CO | N | —CH₂— 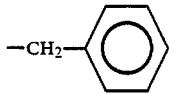 phenyl | 1.5703 |
| 9 | 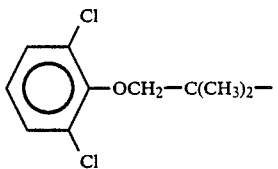 2,6-dichlorophenyl-OCH₂—C(CH₃)₂— | CO | N | —CH₂— 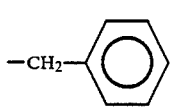 phenyl | viscous oil |
| 10 | 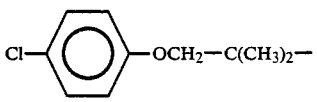 4-chlorophenyl-OCH₂—C(CH₃)₂— | CO | N | —C₄H₉-n | viscous oil |
| 11 | 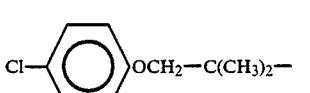 4-chlorophenyl-OCH₂—C(CH₃)₂— | CO | N | —CH₂— 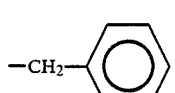 phenyl | 124 |
| 12 | 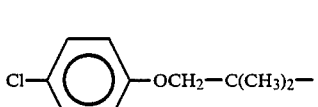 4-chlorophenyl-OCH₂—C(CH₃)₂— | CO | N | —CH₂— 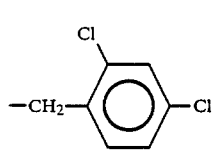 2,4-dichlorophenyl | viscous oil |
| 13 | 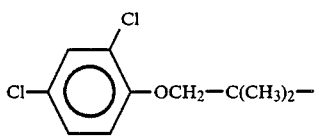 2,4-dichlorophenyl-OCH₂—C(CH₃)₂— | CO | N | —CH₂— 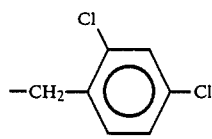 2,4-dichlorophenyl | 110 |
| 14 | 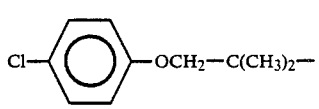 4-chlorophenyl-OCH₂—C(CH₃)₂— | CO | N | —CH₂— 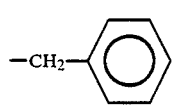 phenyl | 120 |
| 15 | 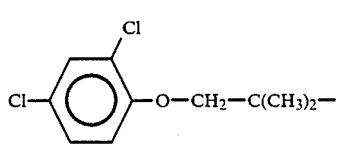 2,4-dichlorophenyl-O—CH₂—C(CH₃)₂— | CO | N | CH₂— 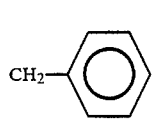 phenyl | 116 |
| 16 | 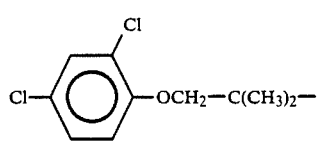 2,4-dichlorophenyl-OCH₂—C(CH₃)₂— | CO | N | —C(CH₃)₃ | 1.5401 |
| 17 | 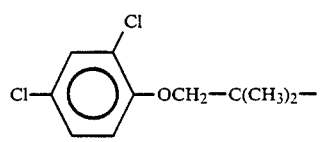 2,4-dichlorophenyl-OCH₂—C(CH₃)₂— | CO | N | —C₄H₉-n | 1.5419 |

-continued

| Example No. | R¹ | X | Y | R² | Melting point (°C.) or $n_D^{20}$ |
|---|---|---|---|---|---|
| 18 | 4-Cl-C₆H₄-SCH₂-C(CH₃)₂- | CO | N | -C₄H₉-n | viscous oil |
| 19 | 4-Cl-C₆H₄-S-CH₂-C(CH₃)₂- | CO | N | -CH₂-C₆H₅ | 136–28 |
| 20 | 4-Cl-C₆H₄-OCH₂-C(CH₃)₂- | CO | N | -CH(CH₃)C₂H₅ | viscous oil |
| 21 | 4-Cl-C₆H₄-OCH₂-C(CH₃)₂- | CO | N | -C₃H₇-i | viscous oil |
| 22 | 2,4-Cl₂-C₆H₃-OCH₂-C(CH₃)₂- | CO | N | -C₂H₅ | viscous oil |
| 23 | 2,6-Cl₂-C₆H₃-OCH₂-C(CH₃)₂- | CO | N | -CH₂-(2,4-Cl₂-C₆H₃) | viscous oil |
| 24 | 4-Cl-C₆H₄-SCH₂-C(CH₃)₂- | CO | N | -C₃H₇-n | 1.5679 |
| 25 | 4-Cl-C₆H₄-SCH₂-C(CH₃)₂- | CO | N | -C₂H₅ | 1.5662 |
| 26 | 4-Cl-C₆H₄-SCH₂-C(CH₃)₂- | CO | N | -CH₃ | 1.5749 |
| 27 | C₆H₅-CH₂-C(CH₃)₂- | CO | N | -C₆H₁₁ (cyclohexyl) | 76–80 (Z-Form) |
| 28 | C₆H₅-CH₂-C(CH₃)₂- | CO | N | -C₆H₁₁ (cyclohexyl) | 63–70 |
| 29 | C₆H₅-CH₂-C(CH₃)₂- | CO | N | -C₆H₁₁ (cyclohexyl) | 87–97 (E-Form) |

-continued
| Example No. | R¹ | X | Y | R² | Melting point (°C.) or $n_D^{20}$ |
|---|---|---|---|---|---|
| 30 | 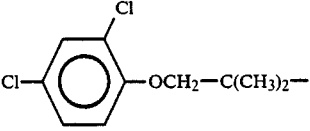 | CO | N |  | viscous oil (Z-Form) |
| 31 | 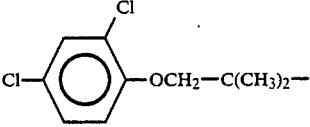 | CO | N |  | viscous oil |
| 32 | 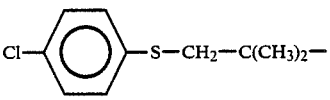 | CO | N |  | viscous oil (Z-Form) |
| 33 | 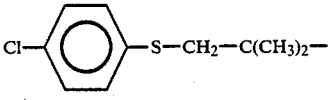 | CO | N |  | viscous oil |
| 34 | 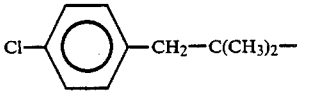 | CO | N |  | viscous oil |
| 35 | 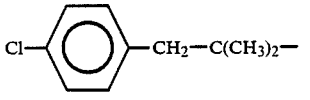 | CO | N |  | viscous oil (E-Form) |
| 36 | 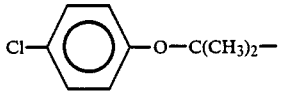 | CO | N | —CH(CH₃)C₂H₅ | 1.5372 |
| 37 | 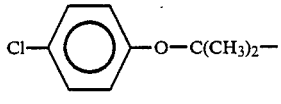 | CO | N | —C₃H₇-n | 1.5421 |
| 38 | 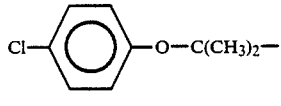 | CO | N | —C₂H₅ | viscous oil |
| 39 | 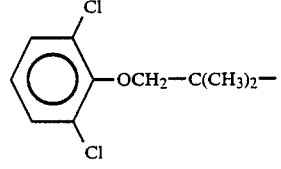 | CH(OH) | N | —C₃H₇-i | viscous oil |
| 40 | 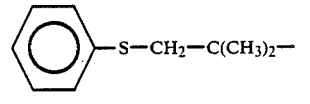 | CH(OH) | N | —C₄H₉-n | viscous oil |
| 41 | 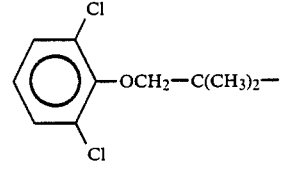 | CH(OH) | N | 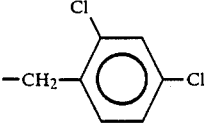 | viscous oil |

-continued

| Example No. | R¹ | X | Y | R² | Melting point (°C.) or $n_D^{20}$ |
|---|---|---|---|---|---|
| 42 | 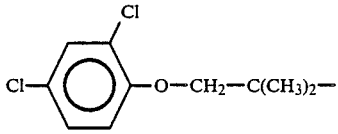 | CH(OH) | N | —C₄H₉-n | 1.5333 |
| 43 | 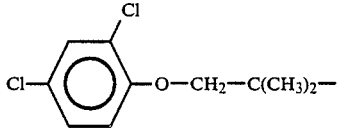 | CH(OH) | N | —C₂H₅ | 30 |
| 44 | 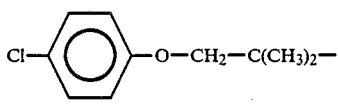 | CH(OH) | N | —CH(CH₃)C₂H₅ | viscous oil |
| 45 | 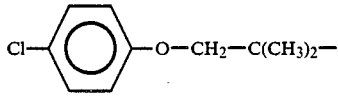 | CO | N | —C₃H₇-i | 30 |
| 46 | 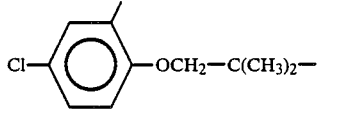 | CH(OH) | N | 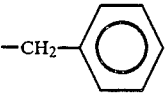 | 54–56 |
| 47 | 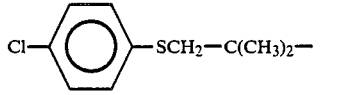 | CH(OH) | N | 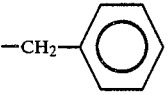 | 120–24 |
| 48 | 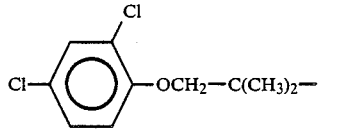 | CH(OH) | N | 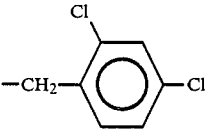 | viscous oil |
| 49 | 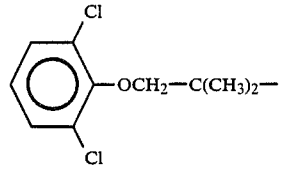 | CH(OH) | N | —C₄H₉-n | viscous oil |
| 50 | C₂H₅—OCH₂—C(CH₃)₂— | CH(OH) | N | —CH₃ | viscous oil |
| 51 | CH₃—OCH₂—C(CH₃)₂— | CH(OH) | N | —CH₃ | viscous oil |
| 52 | C₂H₅—OCH₂—C(CH₃)₂— | CH(OH) | N | —C₃H₇-i | 1.4790 |
| 53 | CH₃—OCH₂—C(CH₃)₂— | CH(OH) | N | —C₃H₇-i | 1.4867 |
| 54 | 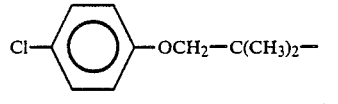 | CH(OH) | N | —C₄H₉-n | viscous oil |
| 55 | 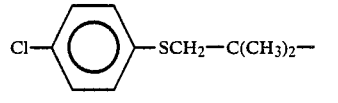 | CH(OH) | N | —C₄H₉-n | viscous oil |
| 56 | 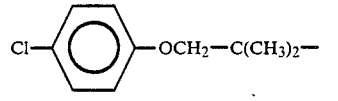 | CH(OH) | N | 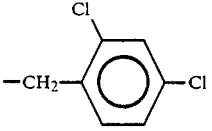 | viscous oil |

-continued

| Example No. | R[1] | X | Y | R[2] | Melting point (°C.) or $n_D^{20}$ |
|---|---|---|---|---|---|
| 57 | 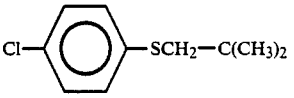 4-Cl-C6H4-SCH2-C(CH3)2- | CH(OH) | N | —C3H7-n | 1.5690 |
| 58 | 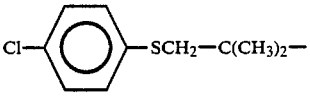 4-Cl-C6H4-SCH2-C(CH3)2- | CH(OH) | N | —CH3 | 1.5638 |
| 59 | 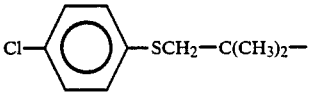 4-Cl-C6H4-SCH2-C(CH3)2- | CH(OH) | N | —C2H5 | 1.5544 |
| 60 | 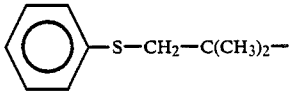 C6H5-S-CH2-C(CH3)2- | CH(OH) | N | 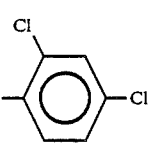 2,4-Cl2-C6H3- | 1.5910 (E-Form) |
| 61 | 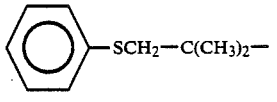 C6H5-SCH2-C(CH3)2- | CH(OH) | N | 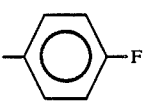 4-F-C6H4- | 139 |
| 62 | 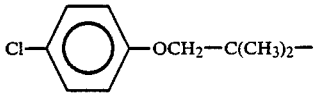 4-Cl-C6H4-OCH2-C(CH3)2- | CH(OH) | N | 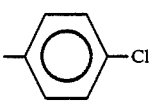 4-Cl-C6H4- | 96(Z-Form) |
| 63 | 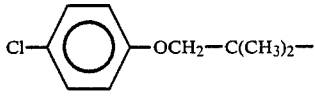 4-Cl-C6H4-OCH2-C(CH3)2- | CH(OH) | N | 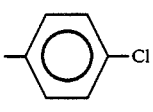 4-Cl-C6H4- | 176(E-Form) |
| 64 | C2H5—OCH2—C(CH3)2— | CH(OH) | N | 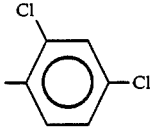 2,4-Cl2-C6H3- | 130(E-Form) |
| 65 | C2H5—OCH2—C(CH3)2— | CH(OH) | N | 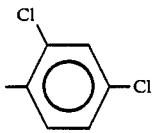 2,4-Cl2-C6H3- | 124 |
| 66 | CH3—OCH2—C(CH3)2— | CH(OH) | N | 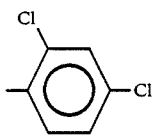 2,4-Cl2-C6H3- | 134(Z-Form) |
| 67 | CH3—OCH2—C(CH3)2— | CH(OH) | N | 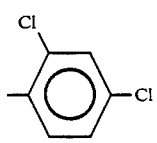 2,4-Cl2-C6H3- | 116(E-Form) |
| 68 | 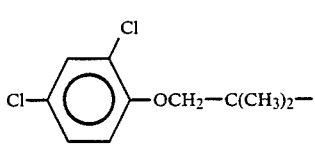 2,4-Cl2-C6H3-OCH2-C(CH3)2- | CH(OH) | N | 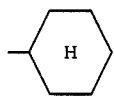 cyclohexyl | viscous oil (Z-Form) |

-continued
| Example No. | R¹ | X | Y | R² | Melting point (°C.) or $n_D^{20}$ |
|---|---|---|---|---|---|
| 69 | 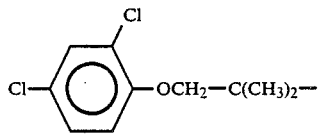 | CH(OH) | N | 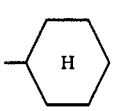 H | amorphous |
| 70 | 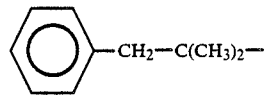 | CH(OH) | N | 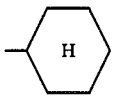 H | viscous oil (E-Form) |
| 71 | 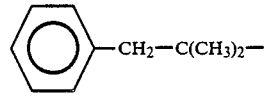 | CH(OH) | N | 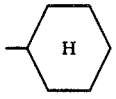 H | viscous oil (Z-Form) |
| 72 | 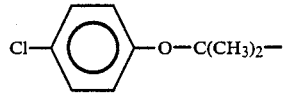 | CH(OH) | N | —$C_2H_5$ | viscous oil |
| 73 | 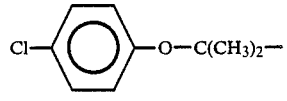 | CH(OH) | N | —$C_3H_7$-n | viscous oil |
| 74 | 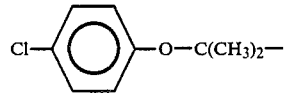 | CH(OH) | N | —$CH(CH_3)C_2H_5$ | viscous oil |
| 75 | $CH_2$=CH—$C(CH_3)_2$— | CH(OH) | N | 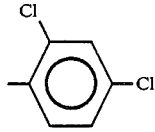 | 128 |
| 76 | 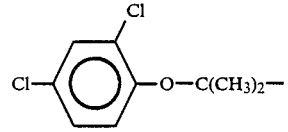 | CH(OH) | N | 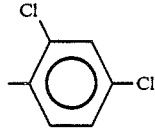 | 136(Z-Form) |
| 77 | NC—$C(CH_3)_2$— | CH(OH) | N | 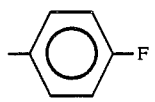 | 220(E-Form) |
| 78 | NC—$C(CH_3)_2$— | CH(OH) | N | 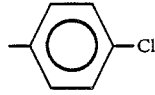 | 194(E-Form) |
| 79 | $CH_2$=CH—$C(CH_3)_2$— | CH(OH) | N | 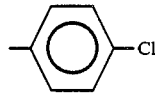 | 128(Z-Form) |
| 80 | $CH_2$=CH—$C(CH_2)_2$— | CH(OH) | N | 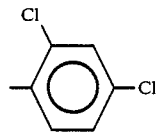 | 128(Z form) |

-continued

| Example No. | R¹ | X | Y | R² | Melting point (°C.) or $n_D^{20}$ |
|---|---|---|---|---|---|
| 81 | Cl—⟨C₆H₄⟩—SCH₂—C(CH₃)₂— | CO | CH | —CH₃ | viscous oil |
| 82 | ⟨C₆H₄⟩(Cl)—SCH₂—C(CH₃)₂— | CO | CH | —C₃H₇-i | viscous oil |
| 83 | Cl—⟨C₆H₄⟩—SCH₂—C(CH₃)₂— | CO | CH | —C₃H₇-n | viscous oil |
| 84 | Cl—⟨C₆H₄⟩—O—C(CH₃)₂— | CO | CH | —C₂H₅ | −1.5595 |
| 85 | Cl,Cl—⟨C₆H₃⟩—OCH₂—C(CH₃)₂— | CO | CH | —C(CH₃)₂ | 1.5463 |
| 86 | Cl,Cl—⟨C₆H₃⟩—OCH₂—C(CH₃)₂— | CO | CH | —CH₃ | 1.5637 |
| 87 | Cl,Cl—⟨C₆H₃⟩—O—CH₂—C(CH₃)₂— | CO | CH | —CH(C₂H₅)—CH₃ | 1.5420 |
| 88 | Cl,Cl—⟨C₆H₃⟩—OCH₂—C(CH₃)₂— | CO | CH | —C₇H₁₅-n | 1.5367 |
| 89 | Cl,Cl—⟨C₆H₃⟩—OCH₂—C(CH₃)₂— | CO | CH | —C₃H₇-i | 1.5511 |
| 90 | Cl—⟨C₆H₄⟩—SCH₂—C(CH₃)₂— | CO | CH | —CH(C₂H₅)—CH₃ | 30 |
| 91 | Cl—⟨C₆H₄⟩—OCH₂—C(CH₃)₂— | CO | CH | —C₃H₇-n | viscous oil |
| 92 | Cl—⟨C₆H₄⟩—OCH₂—C(CH₃)₂— | CO | CH | —CH(C₂H₅)—CH₃ | viscous oil |

-continued

| Example No. | R¹ | X | Y | R² | Melting point (°C.) or $n_D^{20}$ |
|---|---|---|---|---|---|
| 93 | 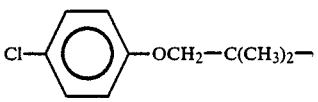 Cl—⬡—OCH₂—C(CH₃)₂— | CO | CH | —C₂H₅ | 53–57 |
| 94 | 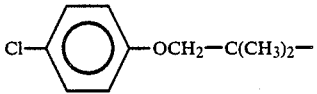 Cl—⬡—OCH₂—C(CH₃)₂— | CO | CH | —C₄H₉-n | viscous oil |
| 95 | 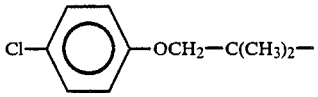 Cl—⬡—OCH₂—C(CH₃)₂— | CO | CH | —C₃H₇-i | viscous oil |
| 96 | 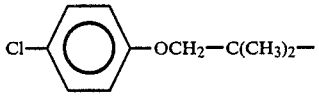 Cl—⬡—OCH₂—C(CH₃)₂— | CH(OH) | CH | —C₃H₇-n | 33 |
| 97 | 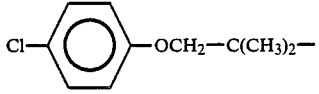 Cl—⬡—OCH₂—C(CH₃)₂— | CH(OH) | CH | —CH(C₂H₅)—CH₃ | 30 |
| 98 | 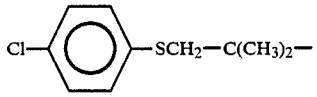 Cl—⬡—SCH₂—C(CH₃)₂— | CH(OH) | CH | —C₃H₇-i | 31 |
| 99 | 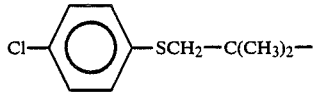 Cl—⬡—SCH₂—C(CH₃)₂— | CH(OH) | CH | —C₃H₇-n | viscous oil |
| 100 | 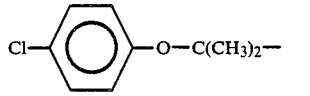 Cl—⬡—O—C(CH₃)₂— | CH(OH) | CH | —C₂H₅ | viscous oil |
| 101 | 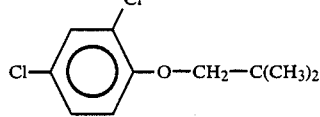 Cl,Cl—⬡—O—CH₂—C(CH₃)₂— | CH(OH) | CH | —C(CH₃)₃ | viscous oil |
| 102 | 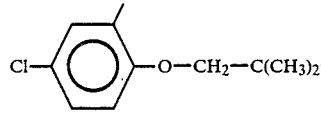 Cl,Cl—⬡—O—CH₂—C(CH₃)₂— | CH(OH) | CH | —CH(CH₃)C₂H₅ | viscous oil |
| 103 | 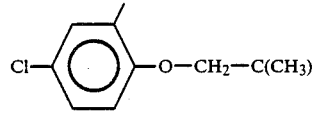 Cl,Cl—⬡—O—CH₂—C(CH₃)₂— | CH(OH) | CH | —CH₃ | 80 |
| 104 | 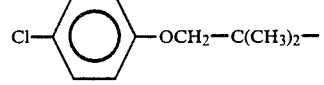 Cl,Cl—⬡—OCH₂—C(CH₃)₂— | CH(OH) | N | —C₃H₇-i | viscous oil |

-continued

| Example No. | R¹ | X | Y | R² | Melting point (°C.) or $n_D^{20}$ |
|---|---|---|---|---|---|
| 105 | 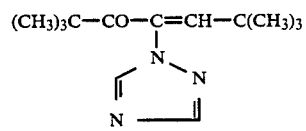 | CH(OH) | CH | —C₇H₁₅-n | viscous oil |
| 106 | 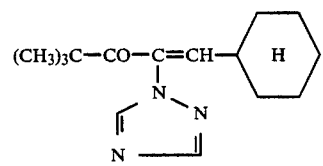 | CO | N | —CH₂CH₂—CH(CH₃)CH₃ with CH₃ | 1.4996 |
| 107 | 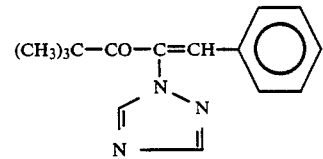 | CH(OH) | N | 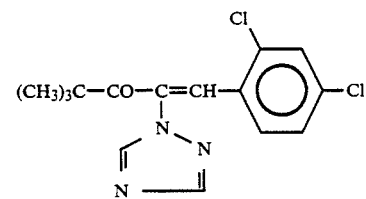 | viscous oil |

E- and Z-form: the two possible geometric isomers

USE EXAMPLES

The compounds shown below are used as comparison substances in the fungicide examples which follow:

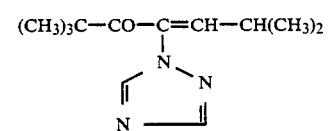 (A)

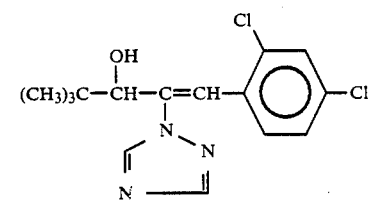 (B)

(CH₃)₃C—CO—C=CH— (phenyl) with triazole (C)

(CH₃)₃C—CO—C=CH— (2,4-dichlorophenyl) with triazole (D)

(CH₃)₃C—CO—C=CH—CH(CH₃)₂ with triazole (E)

OH
|
(CH₃)₃C—CH—C=CH— (2,4-dichlorophenyl) with triazole (F)

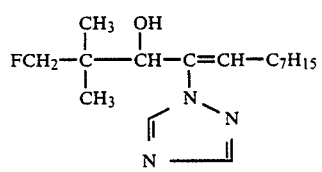 (G)

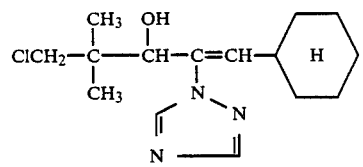 (H)

EXAMPLE A

Venturia test (apply)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the spple scab causative organism (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 54, 57, 2, 59, 33, 3, 70, 71 and 77.

EXAMPLE B

EXAMPLE B
Erysiphe test (barley)/protective
solvent: 100 parts by weight of dimethylformamide Emulsifier: 0.25 parts by weight of alkylaryl polyglycol ester To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 18, 11, 10, 17, 16, 7, 6, 21, 20, 38, 37, 36, 1, 27, 28, 29, 33, 3, 34, 85, 89, 87, 90, 95, 93, 91, 83, 82, 46, 49, 42, 39, 73, 59, 101, 105, 104, 102, 96, 99, 98, 97 and 100.

EXAMPLE C

Puccinia test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 14, 55, 54, 43, 45, 57, 2, 58 and 64.

EXAMPLE D

Cochliobolus sativus test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 24, 57, 2, 58, 59, 93, 82 and 96.

EXAMPLE E

Influence on growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Sugar beet is grown in a greenhouse until formation of the cotyledons is complete. In this stage, the plants are sprayed with the preparation of active compound until dripping wet. After 14 days, the additional growth of the plants is measured and the influence on growth in percent of the additional growth of the control plants is calculated. 0% influence on growth denotes a growth which corresponds to that of the control plants. Negative values characterize an inhibition of growth in comparison to the control plants, while positive values characterize a promotion of growth in comparison to the control plants.

In this test, active compounds 49, 104, 39, 96, 99, 98, 97, 73, 74, 24, 57, 2, 58, 59, 67, 60, 75 and 79 according to the invention exhibit a powerful influence on growth.

EXAMPLE F

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 3 weeks, the additional growth of the plants is measured and the inhibition of growth in percent of the additional growth of the control is calculated. 100 % inhibition of growth means that growth has stopped and 0% denotes a growth corresponding to that of the control plants.

In this test, active compounds 19, 9, 104, 39, 98, 21, 74, 2, 59, 67, 75 and 78 according to the invention exhibit a powerful inhibition of growth.

EXAMPLE G

Stimulation of the fixation of $CO_2$ in soy beans

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. At this stage, the plants are sprayed with the preparations of active compound until dripping wet. In the further course of the experiment, the fixation of $CO_2$ in the plants is determined by customary methods. The values are compared with those of the control plants, which have not been treated with the active compounds.

In this test, active compounds 23, 7, 6, 21 and 36 according to the invention exhibit good stimualtion of the fixation of $CO_2$.

EXAMPLE H

Inhibition of growth of soy beans

Solvent: 30 parts by weight of dimethylformamide

Emulsifier: 1 part by weight of polyoxyethylene sorbitan monolaurate

To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. In this stage, the plants are sprayed with the preparations of active compound until dripping wet. After 3 weeks, the additional growth of all the plants is measured and the inhibition of growth in percent of the additional growth of the control plants is calculated. 100% inhibition of growth means that growth has stopped and 0% denotes a growth corresponding to that of the control plants.

In this test, active compounds 98, 62, 67, 75, 78 and 79 according to the invention exhibit powerful inhibition of growth.

It will be understood that the specification and examples are illustrative but not limitative of the present invention and that other embodiments within the spirit and scope of the invention will suggest themselves to those skilled in the art.

We claim:

1. Azolyl-pentene derivative of the formula $$R-O-(CH_2)_n-\underset{\underset{CH_3}{|}}{\overset{\overset{CH_3}{|}}{C}}-Z-\underset{\underset{R^1}{|}}{C}=CH-R^2$$

in which

R is $C_1-C_{10}$—alkyl, $R^1$ is imidazol-1-yl or 1,2,4-triazol-1-yl, $R^2$ is phenyl, 2-fluorophenyl, 4-fluorophenyl, 2-chlorophenyl, 3-chlorophenyl, 4-chlorophenyl, 2,4-dichlorophenyl, 3,4-dichlorophenyl or 2,4-dichlorophenyl, Z is $$-\underset{\underset{O}{\|}}{C}-$$

or $$-\underset{\underset{OH}{|}}{CH}-,$$

and n is 0 or 1, and its addition salt with an inorganic or organic acid.

2. A substituted azolylvinyl carbinol of the formula $$R^4O-(CH_2)_n-\underset{\underset{CH_3}{|}}{\overset{\overset{CH_3}{|}}{C}}-\underset{}{\overset{\overset{OH}{|}}{CH}}-\underset{\underset{\text{(1,2,4-triazol-1-yl)}}{|}}{C}=CH-R^2$$

in which $R^2$ is phenyl optionally substituted with at least one substituent selected from the group consisting of fluorine and chlorine, $R^4$ is alkyl with 1 to 4 carbon atoms, and n is 0 or 1, or an addition product thereof with an acid or metal salt.

3. A compound according to claim 2, wherein such compound is 1-methoxy-2,2-dimethyl-4-(1,2,4-triazol-1-yl)-5-(2,4-dichlorophenyl)-4-penten-3-ol of the formula $$CH_3-OCH_2-\underset{\underset{CH_3}{|}}{\overset{\overset{CH_3}{|}}{C}}-\underset{}{\overset{\overset{OH}{|}}{CH}}-\underset{\underset{\text{(1,2,4-triazol-1-yl)}}{|}}{C}=CH-\text{(2,4-dichlorophenyl)}$$

or an addition product thereof with an acid or metal salt.

* * * * *

UNITED STATES PATENT AND TRADEMARK OFFICE
CERTIFICATE OF CORRECTION

PATENT NO. : 4,940,798

DATED : July 10, 1990

INVENTOR(S) : Elbe et al.

It is certified that error appears in the above-identified patent and that said Letters Patent is hereby corrected as shown below:

Title Page      FOREIGN PATENT DOCUMENTS: After " 044993 " delete " 3/1982 " and substitute -- 2/1982 --

Col. 38, line 5    Delete second " 2,4- " and substitute 2,6- --

Signed and Sealed this

Fifth Day of May, 1992

Attest:

DOUGLAS B. COMER

*Attesting Officer*      *Acting Commissioner of Patents and Trademarks*